(12) United States Patent
Friedman (10) Patent No.: US 7,465,273 B2
(45) Date of Patent: Dec. 16, 2008

(54) METHOD FOR MONITORING PRE-ECLAMPTIC PATIENTS

(75) Inventor: Bruce A. Friedman, Tampa, FL (US)

(73) Assignee: The General Electric Company, Schenectady, NY (US)

( * ) Notice: Subject to any disclaimer, the term of this patent is extended or adjusted under 35 U.S.C. 154(b) by 0 days.

(21) Appl. No.: 11/948,564

(22) Filed: Nov. 30, 2007

(65) Prior Publication Data
US 2008/0082007 A1    Apr. 3, 2008

Related U.S. Application Data

(62) Division of application No. 11/396,799, filed on Apr. 3, 2006, now Pat. No. 7,344,503.

(51) Int. Cl.
*A61B 5/02* (2006.01)
*A61B 5/08* (2006.01)
*A61B 5/00* (2006.01)

(52) U.S. Cl. .............. 600/494; 600/490; 600/484; 600/532; 600/483; 600/322

(58) Field of Classification Search ............ 600/300, 600/301, 310, 322–324, 326, 328, 335, 481, 600/483–485, 490–503, 529, 532
See application file for complete search history.

(56) References Cited

U.S. PATENT DOCUMENTS

| 5,497,778 A | 3/1996 | Hon |
| 5,558,638 A | 9/1996 | Evers et al. |
| 6,159,147 A | 12/2000 | Lichter et al. |
| 6,416,479 B1 | 7/2002 | Seidman |
| 6,443,906 B1 | 9/2002 | Ting et al. |
| 6,712,762 B1 | 3/2004 | Lichter et al. |
| 6,918,879 B2 | 7/2005 | Ting et al. |

(Continued)

FOREIGN PATENT DOCUMENTS

WO    97/47236 A1    12/1997

(Continued)

OTHER PUBLICATIONS

"A New Noninvasive Parameter", SpCO™—Pulse CO-Oximetry™, Masimo Corporation, pp. 1-4, 2005 (Admitted prior art).

(Continued)

*Primary Examiner*—Charles A Marmor, II
*Assistant Examiner*—Navin Natnithithadha
(74) *Attorney, Agent, or Firm*—Andrus, Sceales, Starke & Sawall, LLP (57) ABSTRACT

A system and method for monitoring and estimating the blood pressure of a pregnant patient that modifies the blood pressure estimating algorithm when the patient is pre-eclamptic. The level of carbon monoxide within a patient's bloodstream or exhaled breath can be analyzed to determine whether a pregnant patient is pre-eclamptic. After the patient has been diagnosed as pre-eclamptic, the NIBP monitoring system adjusts its algorithm for estimating the patient's blood pressure to compensate for the physical changes that occur in the patient during pre-eclampsia. The adjusted blood pressure estimates calculated by the NIBP monitoring system can be calculated using different adjustment techniques and methods and are displayed on the NIBP monitor.

19 Claims, 4 Drawing Sheets

U.S. PATENT DOCUMENTS

| | | |
|---|---|---|
| 6,994,675 B2 | 2/2006 | Sharrock |
| 7,344,503 B2 * | 3/2008 | Friedman .................... 600/494 |
| 2005/0065439 A1 | 3/2005 | Fernando et al. |
| 2006/0178585 A1 | 8/2006 | Sharrock |

FOREIGN PATENT DOCUMENTS

| | | | |
|---|---|---|---|
| WO | 02/30277 A3 | 4/2002 | |

OTHER PUBLICATIONS

"Breath Carbon Monoxide as an Indication of Smoking Habit", Chest®, Mar. 2000, pp. 758-763.

Hemodynamic monitoring high-risk obstetrics patients, II: pregnancy-induced hypertension and preeclampsia. (Cardiovascular Medicine), McCartney, Critical Care Nurse, Oct. 1, 2003.

"Carbon monoxide and hypertension" Joseph F. Ndisang et al., Journal of Hypertension 2004. vol. 22 No. 6, pp. 1057-1074.

"Inflationary oscillometric blood pressure monitoring: validation of the OMRON-MIT", Moneli Golara et al., Blood Pressure Monitoring 2002, vol. 7 No. 6, pp. 325-328.

"Noninvasive measurement of carbon monoxide in the blood—in seconds!", Masimo, www.masimo.com/rad-57 index.htm, Jan. 27, 2005 (Admitted prior art).

"End-tidal carbon monoxide measurements in women with pregnancy-induced hypertension and preeclampsia", Micha Baum, MD et al., Am. J Obstet Gynecol, Oct. 2000, vol. 183 No. 4, pp. 900-903.

* cited by examiner

METHOD FOR MONITORING PRE-ECLAMPTIC PATIENTS

CROSS-REFERENCE TO RELATED APPLICATION

This application is a divisional application of prior U.S. patent application Ser. No. 11/396,799, filed on Apr. 3, 2006, now issued as U.S. Pat. No. 7,344,503, which issued on Mar. 18, 2008.

BACKGROUND OF THE INVENTION

The present invention relates to an automated blood pressure measuring apparatus and method. More specifically, the present invention relates to an automated, non-invasive blood pressure (NIBP) monitor that includes optimized operation for use with pregnant patients, particularly those that are diagnosed as pre-eclamptic, to provide more accurate measurements of the patient's blood pressure.

Automated blood pressure monitoring has rapidly become an accepted and, in many cases, essential aspect of patient care. Such automated monitors are now a conventional part of the patient environment in emergency rooms, intensive and critical care units, and in fetal monitoring systems.

The oscillometric method of measuring blood pressure involves applying an inflatable cuff around an extremity of the patient's body, such as the patient's upper arm. The cuff is inflated to a pressure above the patient's systolic pressure and the cuff pressure is then reduced either continuously or incrementally in a series of small steps. A pressure transducer in communication with the blood pressure cuff measures the cuff pressure, including pressure fluctuations resulting from the beat-to-beat pressure change in the artery under the blood pressure cuff. The data obtained from the pressure transducer is used by a processor within the NIBP monitor to compute the patient's systolic pressure, mean arterial pressure (MAP) and the diastolic pressure.

An example of the oscillometric method of measuring blood pressure is shown and described in U.S. Pat. Nos. 4,360,029; 4,394,034; and 4,638,810, which are commonly assigned with the present invention.

Although NIBP monitors and methods, such as the oscillometric method described above, are effective in determining the blood pressure of a patient, the algorithms used within the processor of the NIBP monitor often provide marginally lower measurements for the blood pressure within high-risk obstetric patients, such as those suffering from pregnancy-induced hypertension and pre-eclampsia. Pregnancy-induced hypertension is hypertension that develops as a consequence of pregnancy and regresses after delivery. Pre-eclampsia is a type of pregnancy-induced hypertension characterized by progressive hypertension and pathological edema.

During pre-eclampsia, the physical characteristics of a patient's vascular system change, which can affect the accuracy of an NIBP monitoring algorithm that was tested in normotensive pregnant patients. As an example, the normal algorithm used to estimate both the systolic and diastolic blood pressure in a patient being monitored by an NIBP system calculates the systolic and diastolic pressures based upon a ratio from the determined mean arterial pressure (MAP). In an obstetric patient suffering from pre-eclampsia, these ratios used to estimate the systolic and diastolic blood pressure in an NIBP monitor tend to result in blood pressure measurements that are slightly lower than the manual blood pressure measurements taken by a physician utilizing a blood pressure cuff and a stethoscope. Since physicians are accustomed to treating patients based upon the manual blood pressure measurements taken using a blood pressure cuff and stethoscope, the underestimation of both the systolic and diastolic pressure when utilizing an automated NIBP monitoring system may not indicate the onset of pre-eclampsia at the same stage as would have been determined utilizing the manual blood pressure cuff and stethoscope determination technique.

Recently, studies have determined that the end tidal carbon monoxide (etCO) levels in pregnant women are lower when the women have gestational hypertension and/or pre-eclampsia as compared to a normotensive pregnant patient. Kreiser, D et al *End tidal carbon monoxide levels are lower in women with gestational hypertension and pre-eclampsia. J Perinatol, Apr.* 1, 2004; 24(4): 213-7. As an example, the etCO values in women suffering from pre-eclampsia were less than or equal 1.6 ppm in 89% of the patients suffering from pre-eclampsia as compared with only 45%, 54% and 46% of non-pregnant, first and third trimester normotensive pregnant women. Thus, the results of the study indicate that the etCO levels in women with gestational hypertension or pre-eclampsia were significantly lower than normotensive pregnant women. Thus, the low levels of carbon monoxide in pregnant women is believed to be an indication of pregnancy-induced hypertension and pre-eclampsia, which can be utilized in addition to a typical blood pressure measurement for a clinician in diagnosing the disorder.

SUMMARY OF THE INVENTION

The following describes a method and system for determining the blood pressure of a patient that has been diagnosed as pre-eclamptic. Preferably, the system includes a non-invasive blood pressure (NIBP) monitoring system as well as a carbon monoxide detection device that provides an indication of the level of carbon monoxide within the patient's expired breath or bloodstream in real time.

The carbon monoxide detection device is operable to determine the carbon monoxide level present within the patient in real time. In one contemplated embodiment, the carbon monoxide detection device is a pulse oximeter sensor modified to determine the level of carboxyhemoglobin (COHb) within the patient's bloodstream. Based upon the level of COHb within the patient's bloodstream, either the carbon monoxide detection device or the processor of the NIBP monitoring system can determine whether the pregnant patient is pre-eclamptic.

Alternatively, the carbon monoxide detection device can be a gas sensing device that determines the end tidal breath CO (etCO) level within the expired breath of the patient. The carbon monoxide detection device can either perform the analysis to determine pre-eclamptic conditions or the processor of the NIBP system can receive the etCO level and determine whether the patient is pre-eclamptic.

Further, the NIBP monitoring system can receive an indication of pre-eclampsia from a remote electronic medical records database that includes other test results that indicate the patient is pre-eclamptic. The pre-eclamptic diagnosis can also be entered into the processor of the NIBP monitoring system manually.

Once the NIBP monitoring system determines that the patient is pre-eclamptic, either through a prior diagnostic finding or the analysis of the carbon monoxide level within the patient, the processor of the NIBP monitoring system adjusts the blood pressure estimates calculated by the NIBP monitoring system using its conventional estimation algorithm. Since the physical characteristics of the blood vessels within a pre-eclamptic pregnant patient are different than a normotensive pregnant patient, the physical condition of the blood vessels effect the blood pressure estimates calculated utilizing the normal blood pressure estimation techniques. Various different methods of adjusting the calculated blood pressure estimates from the NIBP monitoring system are contemplated as being alternative methods for enhancing the operation of the NIBP monitoring system. As an example, fixed offsets may be added to the measured systolic, diastolic and MAP pressure values. Alternatively, offsets that are dependent upon the actual measured systolic, diastolic and MAP pressure values may be utilized. Further, amplitude ratios that are used to determine the systolic and diastolic pressures from the MAP values may be modified when the patient is determined to be pre-eclamptic. Further, offsets may be added to the calculated blood pressure estimate based upon the measured pulse pressures by the pressure transducer within the blood pressure cuff. In any case, the blood pressure estimates calculated utilizing the standard algorithm of the NIBP monitor are modified when the patient has been determined to be pre-eclamptic.

BRIEF DESCRIPTION OF THE DRAWINGS

The drawings illustrate the best mode presently contemplated of carrying out the invention. In the drawings.

DETAILED DESCRIPTION OF THE INVENTION

Figure 1:
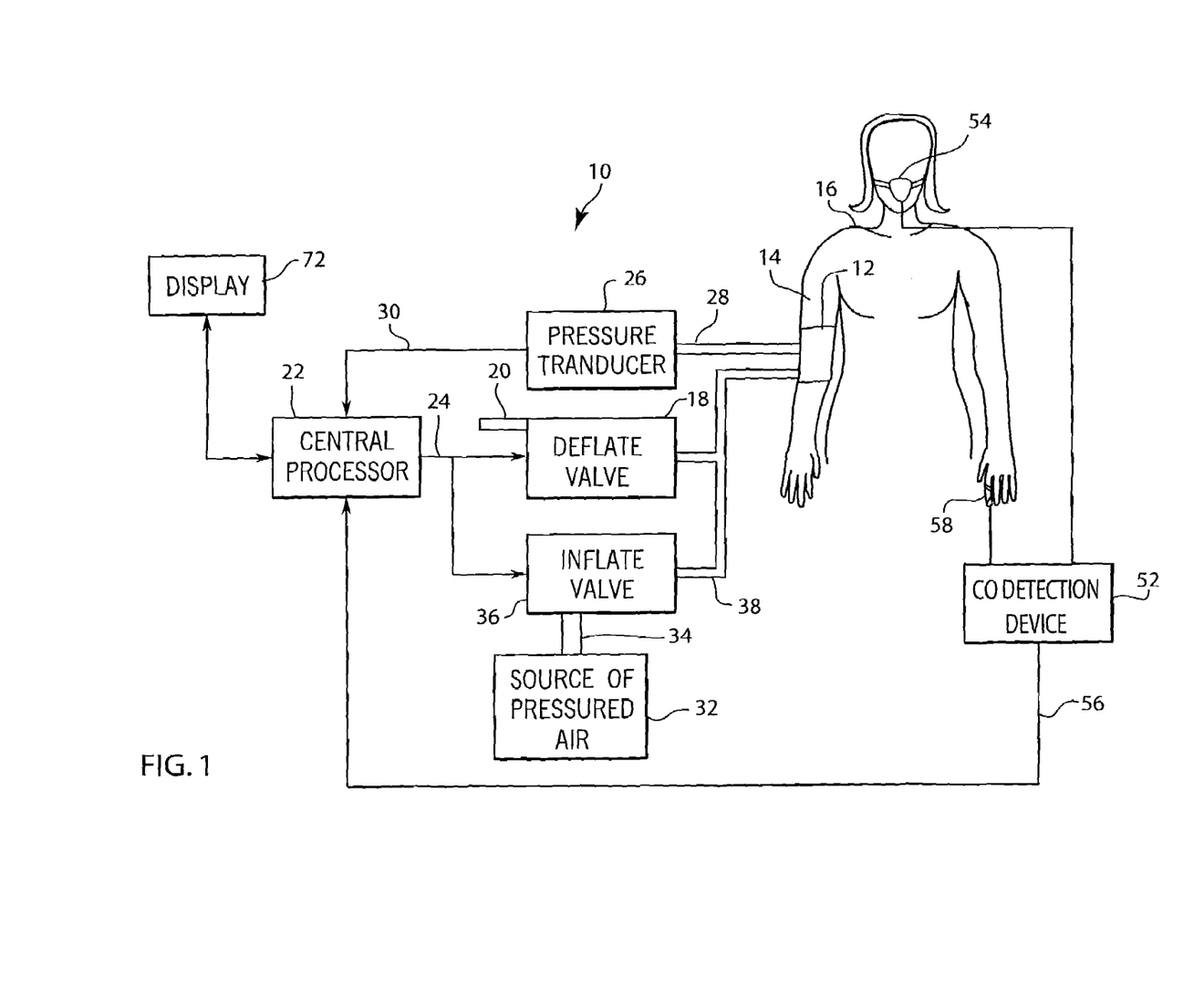
FIG. 1 is a block diagram of a system for monitoring blood pressure utilizing a non-invasive blood pressure (NIBP) monitor and a carbon monoxide detection device.

FIG. 1 generally illustrates a non-invasive blood pressure (NIBP) monitoring system 10 of conventional construction. The NIBP monitoring system 10 includes a blood pressure cuff 12 placed on the arm 14 of a patient 16. The blood pressure cuff 12 can be inflated and deflated for occluding the brachial artery of the patient 16 when in the fully inflated condition. As the blood pressure cuff 12 is deflated using the deflate valve 18 having exhaust 20, the arterial occlusion is gradually relieved. The deflation of the blood pressure cuff 12 by the deflate valve 18 is controlled by a central processor 22 through the control line 24.

A pressure transducer 26 is coupled by duct 28 to the blood pressure cuff 12 for sensing the pressure within the cuff 12. In accordance with conventional oscillometric techniques, the transducer 26 is used to sense pressure oscillations in the cuff 12 that are generated by pressure changes in the brachial artery under the cuff. Thus, the pressure oscillations sensed by the transducer 26 depend upon the physical characteristics of the brachial artery. The electrical signals from the pressure transducer 26 are obtained by the central processor 22, using an analog-to digital converter, through connection line 30.

A source of pressurized air 32 is connected by duct 34 to an inflate valve 36. The inflate valve 36 is connected by duct 38 to the blood pressure cuff 12. The operation of the inflate valve 36 is controlled by the central processor 22 through the control line 24. Thus, the inflation and deflation of the blood pressure cuff 12 is controlled by the central processor 22 through the deflate valve 18 and the inflate valve 36, respectively.

From the standpoint of the principles of the present invention, the processing of the signals from pressure transducer 26 by the central processor 22 to produce blood pressure data, and optionally to reject artifact data, can be conducted in accordance with the prior art teachings of the above-referenced Ramsey '029 and '034 patents. Alternatively, the blood pressure can be determined in accordance with the teachings of Medero et al in U.S. Pat. Nos. 4,543,962, of Medero in 4,546,775, of Hood, Jr. et al in 4,461,266, of Ramsey, III et al in 4,638,810, of Ramsey III et al in 4,754,761, of Ramsey III et al in 5,170,795, of Ramsey III et al in 5,052,397, of Medero in 5,577,508 and of Hersh et al in 5,590,662, all of which are commonly assigned herewith and the disclosures of which are hereby incorporated by reference. In any event, it is desirable to use any of the known techniques to determine the quality of the oscillation complexes received at each cuff pressure so that the blood pressure determination is made using the physiological relevant cuff pressure oscillations from each heart beat and not artifacts.

Figure 2:
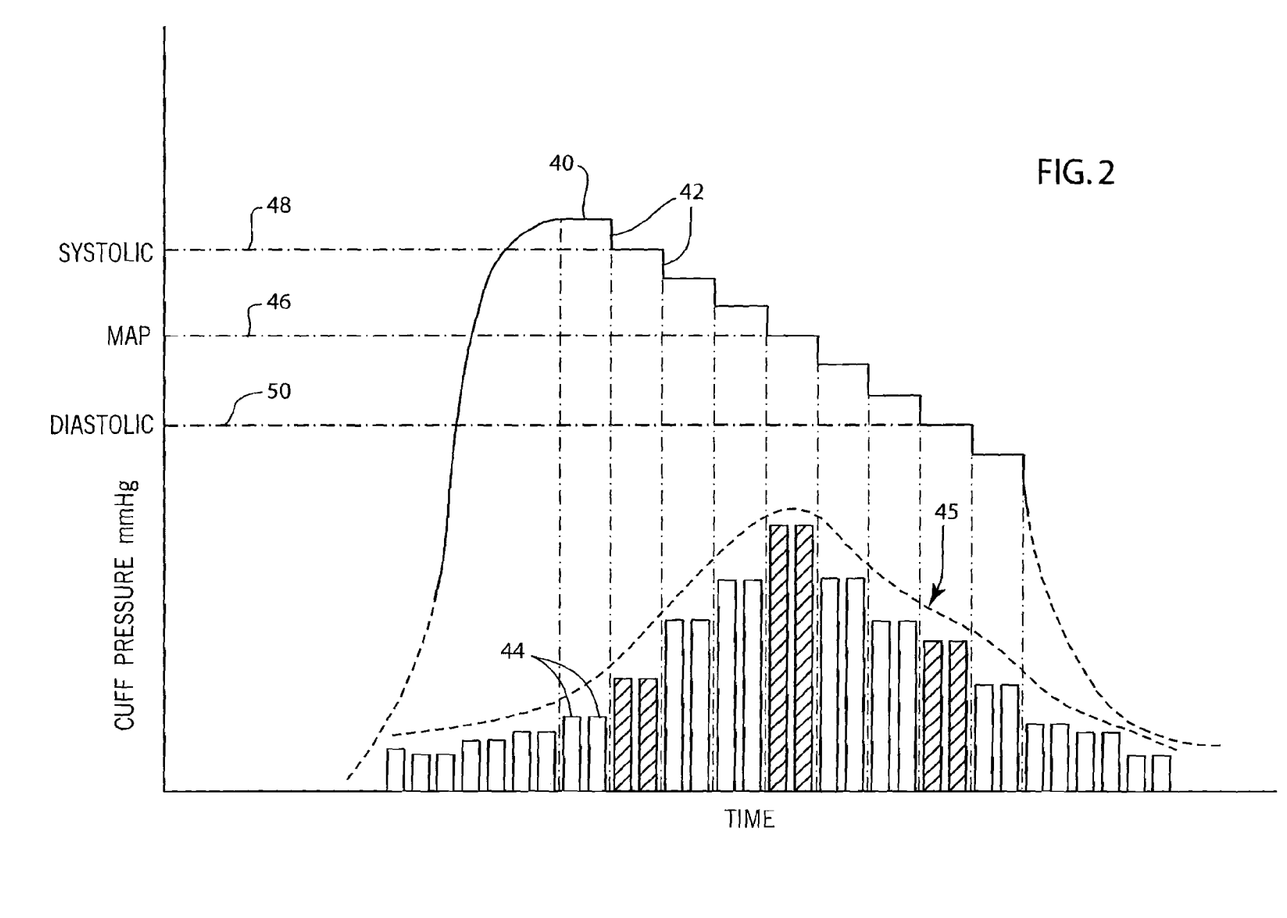
FIG. 2 is a graph depicting the operation of the NIBP monitor to determine at least the systolic, diastolic and mean arterial pressure in a normal patient.

During normal operation of the NIBP monitoring system 10 shown in FIG. 1, the blood pressure cuff 12 is initially placed on the patient 16, typically around the subject's upper arm 14 over the brachial artery. At the inception of the measuring cycle, the blood pressure cuff 12 is inflated to a pressure that fully occludes the brachial artery, i.e., prevents blood from flowing through the brachial artery at any point in the heart cycle. In FIG. 2, the initial inflation pressure is illustrated by reference number 40.

After the blood pressure cuff has been inflated to the initial inflation pressure 40, the deflate valve is actuated by the central processor to deflate the cuff in a series of pressure steps 42. Although various values for each pressure step 42 can be utilized, in one embodiment of the invention, the pressure step 42 is about 8 mm Hg per step.

After each pressure step 42, the NIBP monitoring system detects and records one or more pressure oscillations 44 for the current cuff pressure level. The pressure transducer measures the internal cuff pressure and provides an analog signal characterizing the blood pressure oscillatory complexes. The peak values of the complex signals are determined within the central processor.

As the measurement cycles progress, the peak amplitude of the blood pressure complexes generally become monotonically larger to a maximum and then become monotonically smaller as the cuff pressure continues toward full deflation, as illustrated by the bell-shaped graph 45 in FIG. 2. The peak amplitude of the cuff pressure oscillation complexes, and the corresponding occluding-cuff pressure values, are retained in the central processor memory. The oscillometric measurements are used by an algorithm in the central processor to calculate the mean arterial pressure (MAP) 46, the systolic pressure 48 and the diastolic pressure 50 in a known manner.

In typical NIBP monitoring systems that utilized the detected pressure oscillations 44 to calculate the systolic pressure 48 and the diastolic pressure 50, these blood pressure estimates are based upon the maximum amplitude of the pressure oscillations, which signify the mean arterial pressure 46. Once the mean arterial pressure 46 has been calculated, the systolic pressure is typically estimated as a ratio of the MAP 46. As an example, the systolic pressure 48 is determined to be the cuff pressure at the detected pressure oscillation having an amplitude of ½ the maximum pressure oscillation. Likewise, the diastolic pressure 50 is set to be the cuff pressure past the peak oscillation at which the amplitude of the pressure oscillation is ⅝ the value of the maximum pressure oscillation. The use of these two ratios to estimate the systolic and diastolic pressure based upon the detected MAP provides very accurate blood pressure estimations for normotensive patients.

In the normal operation of an NIBP monitor using oscillometric methods of measuring the blood pressure, the pressure transducer 26 receives signals from the blood pressure cuff that are, in part, based upon the physical characteristics of the arteries within the patient being monitored. The blood vessels within the patient function as a pressure sensor in transferring pressure pulses that relate to the blood pressure in the patient. If the physical characteristics of the blood vessels within the patient are altered, such as during pre-eclampsia, the pressure pulses detected by the pressure transducer are altered as compared to those from a normotensive patient. Since the physical characteristics of the patient's blood vessels change during pre-eclampsia, the normal algorithm used to estimate the systolic and diastolic blood pressures may be inaccurate. Typically, the blood pressure estimates determined utilizing the typical algorithm from an NIBP monitor result in systolic and diastolic blood pressure estimates that are slightly lower than the systolic and diastolic blood pressure measurements made by a physician utilizing manual measurement technique, such as with a blood pressure cuff and stethoscope. Since physicians typically treat patients based upon these manual measurements, the use of the typical NIBP monitoring algorithm may result in lower blood pressure estimates, thus causing an altered course of treatment.

Referring now to FIG. 1, the monitoring system of the present invention utilizes a carbon monoxide detection device 52 to detect the level of carbon monoxide within the patient's bloodstream as an indication of pre-eclampsia. In the embodiment shown in FIG. 1, the carbon monoxide detection device 52 can be one of several different, alternate devices utilized to detect the level of carbon monoxide within the patient. The first proposed carbon monoxide detection device utilizes a patient mask 54 to receive expired gases from the patient. The expired gases received by the patient mask 54 are analyzed by the carbon monoxide detection device 52 and an end tidal breath CO (etCO) level is delivered to the central processor 22 of the NIBP monitoring system 10 along the control line 56. Once the central processor 22 receives the etCO level from the carbon monoxide detection device 52, the central processor 22 can compare the etCO level to pre-selected limits to determine whether the patient 16 is pre-eclamptic. Alternatively, the CO detection device 52 can include internal software to determine whether the patient is pre-eclamptic and deliver this information to the processor 22.

In addition to utilizing a carbon monoxide detection device that receives the expired gases from the patient, the carbon monoxide detection device 52 could also be a pulse CO-oximetry device that utilizes a finger probe 58 to estimate the level of carbon monoxide in the patient's blood. Specifically, the carbon monoxide detection device 52 that utilizes the finger probe 58 estimates the carboxyhemoglobin (COHb) level within the patient non-invasively utilizing a modified pulse oximeter, such as the RAD-57 Pulse CO Oximeter available from Massimo. In this type of system, the carbon monoxide detection device 52 generates a signal along the control line 56 indicating the COHb level within the patient 16. Upon receiving the COHb level, the central processor 22 can determine whether the patient 16 is pre-eclamptic. Alternatively, the CO detection device 52 can include internal software to determine whether the patient is pre-eclamptic and deliver this information to the processor 22.

Although two different alternate types of carbon monoxide detection devices 52 are described above as being proposed alternatives, it should be understood that various other alternate carbon monoxide detection devices 52 are contemplated as being within the scope of the present invention. Additionally, although the carbon monoxide detection device 52 is shown separate from the central processor 22, it is contemplated that the functionality of the carbon monoxide detection device 52 could be incorporated within the NIBP monitoring system 10 such that the inputs from either the patient mask 54 or the finger probe 58 could be directly received by the central processor 22, rather than requiring the intermediate carbon monoxide detection device 52.

Figure 3:
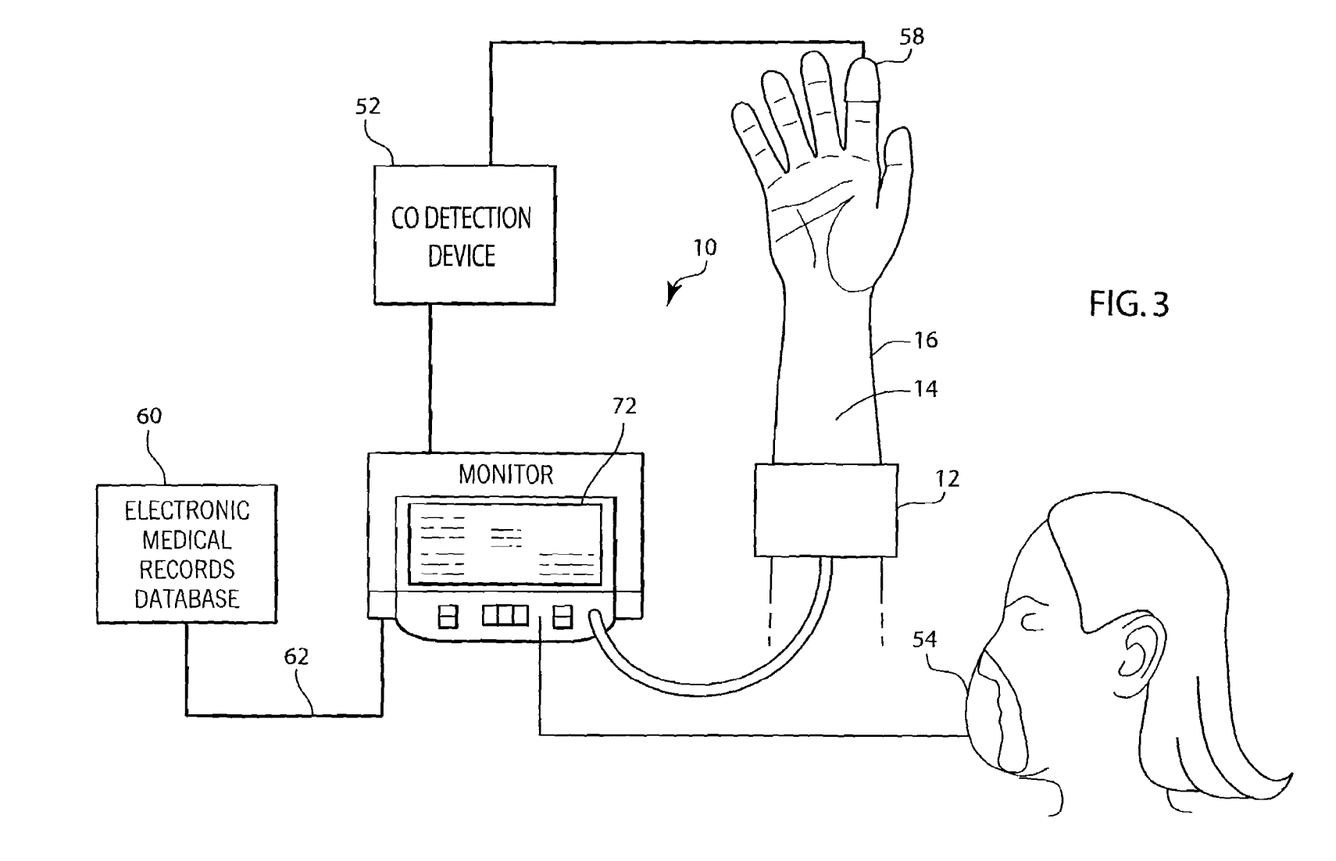
FIG. 3 is a schematic illustration of the use of a carbon monoxide detection device along with the NIBP monitor.

Referring now to FIG. 3, the NIBP monitoring system 10 is shown connected to the carbon monoxide detection device 52 to receive information relating to the carbon monoxide levels within the patient 16. In this manner, the NIBP monitoring system 10 can determine whether the patient is pre-eclamptic, as described above. In addition, the NIBP monitor 10 is shown connected to an electronic medical records database 60 through a control line 62, which may be a hardwire connection or a wireless network connection. In this manner, the NIBP monitoring system 10 can communicate with the electronic medical records database 60 to receive information relating to the patient 16. For example, the NIBP monitoring system 10 can receive information indicating that the patient 16 is pre-eclamptic based upon a prior diagnosis. Although high blood pressure and reduced levels of carbon monoxide are both indicators of pre-eclampsia, various other clinical information, such as protein levels within the urine, are also indicators of pre-eclampsia within a patient. Thus, if the patient has been diagnosed as pre-eclamptic based upon other test results, the pre-eclampsia diagnosis can be received by the NIBP monitoring system 10 from the records database 60.

Alternatively, the NIBP monitor also includes input keys that allow a physician to manually enter an indication that the patient 16 is pre-eclamptic based upon various other test results. Thus, the NIBP monitoring system 10 can determine that a patient is pre-eclamptic based upon either direct measurements from the patient's exhaled breath, a modified pulse oximeter measurement from a finger probe, a diagnosis received from an electronic medical records database, or based upon a medical entry from a clinician directly into the NIBP monitor. Although these different alternate methods of receiving a pre-eclamptic diagnosis are contemplated, it should be understood that other alternate methods are contemplated as being within the scope of the present invention.

Figure 4:
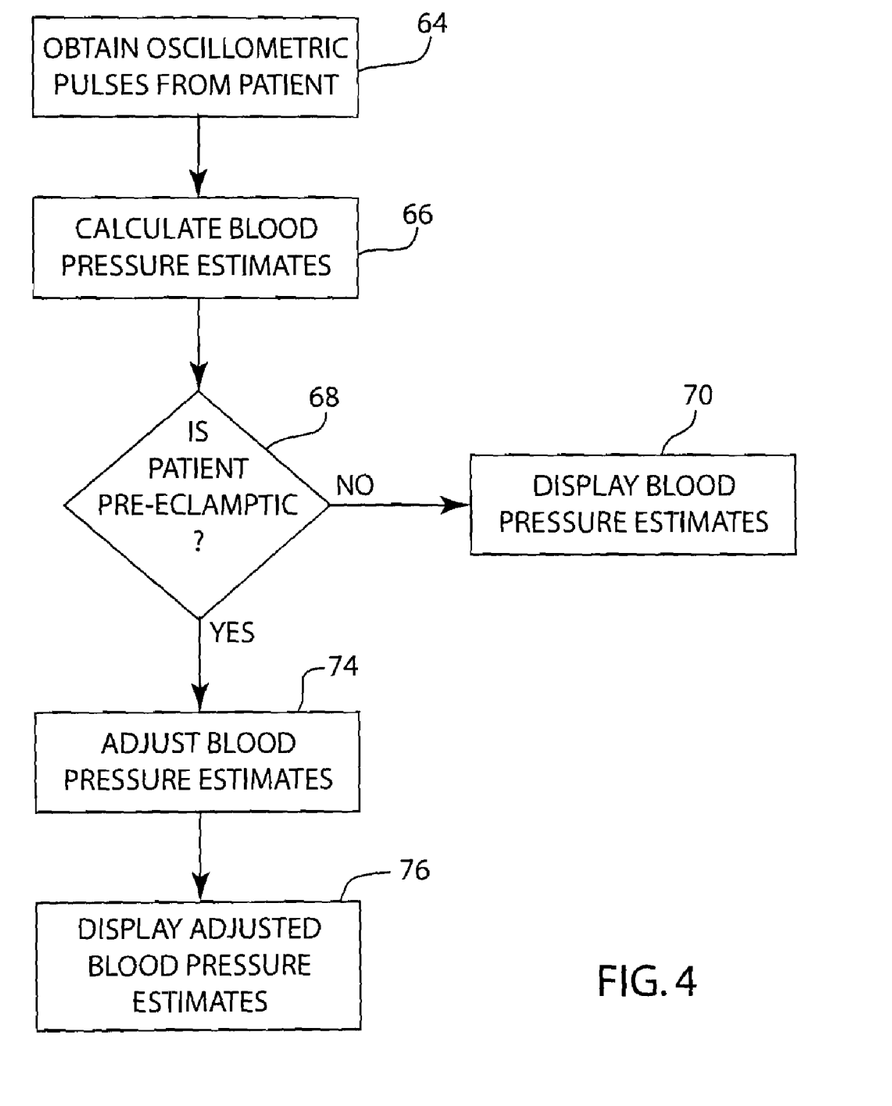
FIG. 4 is a flowchart illustrating the use of the carbon monoxide detection device with the NIBP monitor to adjust the blood pressure estimates for a patient with pregnancy-induced hypertension or pre-eclampsia.

Referring now to FIG. 4, the method of operating the NIBP monitoring system will now be described. As illustrated in FIG. 4, the first step in the process is for the NIBP monitoring system to obtain the oscillometric pulses from the patient as the blood pressure cuff pressure is stepped down from the initial inflation pressure to a final inflation pressure, as indicated in step 64. Once the oscillometric pulses have been received from the patient, the processor of the NIBP monitor can then calculate the typical blood pressure estimates in step 66 using its conventional algorithm. As indicated previously, the conventional algorithm utilized in many NIBP monitoring systems determines the systolic and diastolic pressure based upon a ratio of the maximum oscillation amplitude that corresponds to the mean arterial pressure.

Once the processor of the NIBP monitoring system has calculated the blood pressure estimates in step 66, the processor then determines in step 68 whether the patient is pre-eclamptic or suffering from pregnancy-induced hypertension. As described previously, the processor can make this determination based upon either a signal from a carbon monoxide detection device, a previous diagnosis received from an electronic medical records database, or based upon a manual entry made by the physician into the NIBP monitoring system. In each case, the processor of the NIBP monitor must determine whether the patient is pre-eclamptic in step 68 and then modifies the normal blood pressure estimates based upon the determination.

If the processor determines in step 68 that the patient is not pre-eclamptic, the processor displays the blood pressure estimates calculated in step 66 on the monitor display 72 shown in FIG. 3. Once the blood pressure estimates have been displayed in step 70, the system returns to step 64 to again obtain the oscillometric pulses from the patients on a regular interval. As an example, the oscillometric pulses from the patient may be obtained every fifteen minutes or at intervals determined by the physician.

If, however, the processor determines in step 68 that the patient is pre-eclamptic, the system then adjusts the blood pressure estimates in step 74. As described previously, when a patient is pre-eclamptic, the blood pressure estimates determined in step 66 are often low for both the systolic and diastolic pressure estimates as compared to the blood pressure manually determined by a physician using a blood pressure cuff and a stethoscope. In accordance with the present invention, the processor adjusts the blood pressure estimates in step 74 such that the blood pressure estimates more accurately correspond to manual blood pressure measurements typically taken by a physician utilizing a manually inflatable blood pressure cuff and stethoscope.

Various different methods are contemplated as being within the scope of the present invention to adjust the blood pressure estimate in step 74. Several presently contemplated methods are set forth below as illustrative examples but are not meant to provide an exhaustive listing of all the different types of methods that could be contemplated as being within the scope of the present invention.

A first contemplated method of adjusting the blood pressure estimates is to add a fixed offset to the estimated systolic, diastolic and MAP pressure values. The fixed offsets can be determined utilizing historic data values comparing the blood pressure estimates generated by the NIBP monitoring system on pre-eclamptic patients as compared to the manual blood pressure values determined by a physician utilizing a manually inflatable blood pressure cuff and stethoscope. Based upon these historic values, fixed offsets can be determined and added to the systolic, diastolic and MAP pressure values calculated in step 66. The adjusted blood pressure estimate would then be displayed in step 76.

In a second, alternate method of adjusting the blood pressure estimates, the processor of the NIBP monitoring system can add offsets to the calculated blood pressure estimates that are dependent upon the value of the measured systolic, diastolic and/or MAP pressure values. As an example, the adjusted systolic pressure may be calculated as 125% of the calculated systolic pressure estimate from step 66. Likewise, the adjusted diastolic pressure may be selected at 125% of the diastolic blood pressure estimate determined in step 66. In this method of adjusting the blood pressure estimates, the amount of offset is dependent upon the calculated blood pressure estimates and the amount of offset will thus vary depending upon the measured blood pressure from the patient. Once again, once the adjusted blood pressure estimates have been determined, the adjusted blood pressure estimates are displayed in step 76.

As a third contemplated method of adjusting the blood pressure estimates, the processor of the NIBP monitoring system may adjust the amplitude ratios used to determine the systolic and diastolic pressures in step 66. As described previously, many NIBP monitoring systems determine the systolic and diastolic pressures based upon a ratio of the amplitude of the maximum oscillation pulse, which corresponds to the mean arterial pressure. As an example, many NIBP monitoring systems calculate the systolic pressure as the cuff pressure at which the amplitude of the measured oscillation pulse is ½ the amplitude of the maximum oscillation pulse. In this contemplated method of adjusting the blood pressure estimates, the standard ratio of ½ utilized to calculate the systolic pressure from the maximum oscillation amplitude and may be modified to ⅝. Since the ratio has been increased, the systolic blood pressure estimate will also be increased. Further, the diastolic pressure is typically determined as the cuff pressure at which the amplitude of the pressure oscillations is ⅝ the maximum amplitude of the pressure oscillations. This ratio will also be increased, such as to $^{11}/_{16}$, to again adjust the calculated diastolic pressure based upon the amplitudes of the oscillation pulses. Once again, once the adjusted blood pressure estimates are calculated, the adjusted blood pressure estimates are displayed in step 76 such that the physician is presented only with the adjusted blood pressure estimates and does not view the calculated blood pressure estimates determined in step 66.

A fourth alternate method of adjusting the blood pressure estimates includes adding offsets to the blood pressure estimates based upon the measured pulse pressures at the systolic and diastolic values. Since the oscillation pulses are the physical characteristics actually measured by the NIBP monitoring system, adding an offset to the pulse pressure allows the system to compensate the actual physical measurements taken by the system rather than modify the calculations determined by the system. Again, once the adjusted blood pressure estimates are calculated, the adjusted blood pressure estimates are displayed in step 76.

Once the system has displayed the adjusted blood pressure estimates, the system returns to the beginning of the cycle to obtain the oscillometric pulses from the patient. Referring back to FIGS. 1 and 3, the use of the carbon monoxide detection device 52 with the conventional NIBP monitoring system allows the NIBP monitoring system to make a diagnosis of pre-eclampsia based upon carbon monoxide levels detected in real time from the patient. Once the NIBP monitoring system determines that the patient is pre-eclamptic, the processor within the NIBP monitoring system can adjust the algorithm used to calculate at least the systolic and diastolic pressures from the patient such that the NIBP monitoring system more accurately displays blood pressure for patients that are pre-eclamptic. It is contemplated that the carbon monoxide detection device can detect the level of carbon monoxide in a patient using one of multiple different detection techniques, such as detecting the level of carbon monoxide in an exhaled patient breath or detecting the level of COHb within a patient's bloodstream, utilizing a finger probe. The use of the carbon monoxide detection device 52 allows the pre-eclampsia determination to be made in real time based upon patient parameters that are obtained in synchronization with the calculation of the patient blood pressure. Once the NIBP monitor determines that the patient is pre-eclamptic, the processor within the NIBP monitoring system can adjust its algorithm to more accurately provide an indication of the patient's blood pressure.

I claim:

1. A method of enhancing the operation of a non-invasive blood pressure (NIBP) monitor having a blood pressure cuff selectively inflatable and deflatable to determine at least a systolic pressure, a mean arterial pressure and a diastolic pressure for a patient, the method comprising the steps of:
- receiving an indication that the patient is pregnant at the NIBP monitor;
- receiving an indication that the patient is pre-eclamptic at the NIBP monitor;
- adjusting at least the determined systolic pressure and the determined diastolic pressure to compensate for the effects of pre-eclampsia; and
- displaying the adjusted blood pressure estimates.

2. The method of claim 1 further comprising the steps of:
- receiving an indication of the carbon monoxide level in the blood of the patient at the NIBP monitor; and
- determining whether the patient is pre-eclamptic based upon the carbon monoxide level.

3. The method of claim 2 further comprising the steps of:
- positioning a carbon monoxide detection device on the patient to detect the level of carbon monoxide in the patient's blood;
- generating a signal related to the carbon monoxide level; and
- receiving the signal at the NIBP monitor.

4. The method of claim 3 wherein the carbon monoxide detection device is a pulse oximeter that detects the carboxyhemoglobin (COHb) level in the patient's blood.

5. The method of claim 3 wherein the carbon monoxide detection device detects the level of carbon monoxide in the patient's expired breath.

6. The method of claim 1 wherein the step of adjusting the blood pressure estimates includes:
- increasing the estimated systolic pressure by a first offset value when the patient is pre-eclamptic; and
- increasing the estimated diastolic pressure by a second offset value when the patient is pre-eclamptic.

7. The method of claim 1 wherein the step of adjusting the blood pressure estimates includes:
- adjusting the ratio of the systolic pressure from an estimated mean arterial pressure when the patient is pre-eclamptic; and
- adjusting the ratio of the diastolic pressure from the mean arterial pressure when the patient is pre-eclamptic.

8. A method of enhancing the operation of a non-invasive blood pressure (NIBP) monitor having a blood pressure cuff selectively inflatable and deflatable to determine at least a systolic pressure, a mean arterial pressure and a diastolic pressure for a patient, the method comprising the steps of:
- receiving an indication that the patient is pre-eclamptic at the NIBP monitor;
- adjusting at least the determined systolic pressure and the determined diastolic pressure to compensate for the effects of pre-eclampsia; and
- displaying the adjusted systolic and diastolic pressure estimates.

9. The method of claim 8 wherein the step of adjusting the blood pressure estimates includes:
- increasing the estimated systolic pressure by a first offset value when the patient is pre-eclamptic; and
- increasing the estimated diastolic pressure by a second offset value when the patient is pre-eclamptic.

10. The method of claim 8 wherein the step of adjusting the blood pressure estimates includes:
- adjusting the ratio of the systolic pressure from an estimated mean arterial pressure when the patient is pre-eclamptic; and
- adjusting the ratio of the diastolic pressure from the mean arterial pressure when the patient is pre-eclamptic.

11. The method of claim 8 wherein the pre-eclamptic indication is manually received at the NIBP monitor.

12. The method of claim 8 wherein the pre-eclamptic indication is received from a remote data storage system in communication with the NIBP monitor.

13. The method of claim 12 wherein the remote data storage system is an electronic database including historical information related to the patient.

14. A method of enhancing the operation of a non-invasive blood pressure (NIBP) monitor having a blood pressure cuff selectively inflatable and deflatable to determine at least a systolic pressure, a mean arterial pressure and a diastolic pressure for a patient, the method comprising the steps of:
- receiving an indication of the carbon monoxide level in the blood of the patient at the NIBP monitor;
- determining whether the patient is pre-eclamptic based upon the carbon monoxide level;
- adjusting at least the determined systolic pressure and the determined diastolic pressure to compensate for the effects of pre-eclampsia; and
- displaying the adjusted blood pressure estimates.

15. The method of claim 14 further comprising the steps of:
- positioning a carbon monoxide detection device on the patient to detect the level of carbon monoxide in the patient's blood;
- generating a signal related to the carbon monoxide level; and
- receiving the signal at the NIBP monitor.

16. The method of claim 15 wherein the carbon monoxide detection device is a pulse oximeter that detects the carboxyhemoglobin (COHb) level in the patient's blood.

17. The method of claim 15 wherein the carbon monoxide detection device detects the level of carbon monoxide in the patient's expired breath.

18. The method of claim 14 wherein the step of adjusting the blood pressure estimates include:
- increasing the estimated systolic pressure by a first offset value when the patient is pre-eclamptic; and
- increasing the estimated diastolic pressure by a second offset value when the patient is pre-eclamptic.

19. The method of claim 14 wherein the step of adjusting the blood pressure estimates include:
- adjusting the ratio of the systolic pressure from an estimated mean arterial pressure when the patient is pre-eclamptic; and
- adjusting the ratio of the diastolic pressure from the mean arterial pressure when the patient is pre-eclamptic.

* * * * *